US012629285B1

(12) United States Patent
Parry

(10) Patent No.: US 12,629,285 B1
(45) Date of Patent: May 19, 2026

(54) GLOW IN THE DARK EARPLUGS

(71) Applicant: Strand Industries LLC, Woodland Hills, CA (US)

(72) Inventor: Ryan Parry, Los Angeles, CA (US)

(73) Assignee: Strand Industries LLC, Woodland Hills, CA (US)

( * ) Notice: Subject to any disclaimer, the term of this patent is extended or adjusted under 35 U.S.C. 154(b) by 0 days.

(21) Appl. No.: 18/951,293

(22) Filed: Nov. 18, 2024

(51) Int. Cl.
*A61F 11/08* (2006.01)
*C08G 77/04* (2006.01)
*C08K 3/105* (2018.01)

(52) U.S. Cl.
CPC ............ *A61F 11/085* (2022.01); *C08G 77/04* (2013.01); *C08K 3/105* (2018.01)

(58) Field of Classification Search
CPC ........ A61F 11/08; A61F 11/085; A61F 11/06; A61F 11/30; A61F 11/14; H04R 1/1083; H04R 25/65; H04R 25/652; C08K 3/105; C08G 77/04
See application file for complete search history.

(56) References Cited

U.S. PATENT DOCUMENTS 8,509,453 B2    8/2013  Bychkov
9,803,582 B2    10/2017  Clacken

FOREIGN PATENT DOCUMENTS

| CN | 102690510 A | * | 9/2012 | |
|---|---|---|---|---|
| CN | 108670554 A | * | 10/2018 | ............... A61N 5/00 |
| DE | 102017217718 A1 | * | 4/2019 | ........ B29C 33/3835 |
| JP | 2000350298 A | * | 12/2000 | |

* cited by examiner

*Primary Examiner* — Ophelia A Hawthorne
(74) *Attorney, Agent, or Firm* — Nolan Heimann LLP; Adam Diament

(57) ABSTRACT

An earplug includes a body made of a silicone material containing a phosphorescent material that causes the earplug to glow in the dark after exposure to light. A filter for reducing sound is positioned within the body. The silicone material includes 80-90% polydimethylsiloxane and 5-15% of the phosphorescent material, such as zinc sulfide, strontium aluminate, or rare-earth metal chelates. A fin extends from the body and fits into folds of an outer ear to secure the earplug in place. The body has a layered design with multiple sections that gradually decrease in diameter toward a tip of the earplug.

9 Claims, 3 Drawing Sheets

GLOW IN THE DARK EARPLUGS

CROSS-REFERENCE TO RELATED APPLICATIONS

None.

FIELD OF INVENTION

The present disclosure relates to earplugs, and more particularly to glow-in-the-dark silicone earplugs incorporating phosphorescent materials for visibility in low-light conditions without the need for batteries.

BACKGROUND

Earplugs have become increasingly popular for health and safety reasons, in order reduce the decibles entering a person's ear. Traditional earplugs are typically made from materials such as silicone or foam, chosen for their comfort and ability to create a seal within the ear canal.

As the use of earplugs has grown, so too has the desire for additional features that enhance their functionality and user experience. One area of interest has been the development of earplugs that are easily locatable in low-light conditions. This is particularly relevant as earplugs are often small and can be easily misplaced or dropped in dimly lit environments.

Various approaches have been explored to address the issue of earplug visibility in low-light conditions. Some solutions have involved the integration of active light-emitting components, such as LEDs, into the earplug design. However, these approaches typically require a power source, such as batteries, which can add weight, complexity, and maintenance requirements to the earplugs.

As the demand for multifunctional and user-friendly personal audio devices continues to grow, there remains a need for innovative solutions that can enhance the usability and convenience of earplugs without compromising their primary audio functions or user comfort.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

The present disclosure provides an earplug device comprising a body made of a silicone material. The silicone material incorporates a phosphorescent material that causes the earplug to glow in the dark after being exposed to light. The earplug device also includes a sound-impeding filter positioned within the body.

A method of using an earplug device is also disclosed. The method involves exposing an earplug device to light, wherein the earplug device comprises a body made of a silicone material incorporating a phosphorescent material. The method further includes inserting the earplug device into an ear canal and blocking sound using a sound-impeding filter positioned within the body of the earplug device.

Additionally, the disclosure presents a method of manufacturing an earplug device. The method comprises mixing a silicone material with a phosphorescent material to form a mixture, molding the mixture into an earplug body shape, and curing the molded mixture.

The foregoing general description of the illustrative embodiments and the following detailed description thereof are merely exemplary aspects of the teachings of this disclosure and are not restrictive.

BRIEF DESCRIPTION OF FIGURES

Non-limiting and non-exhaustive examples are described with reference to the following figures.

DETAILED DESCRIPTION

Figure 1:
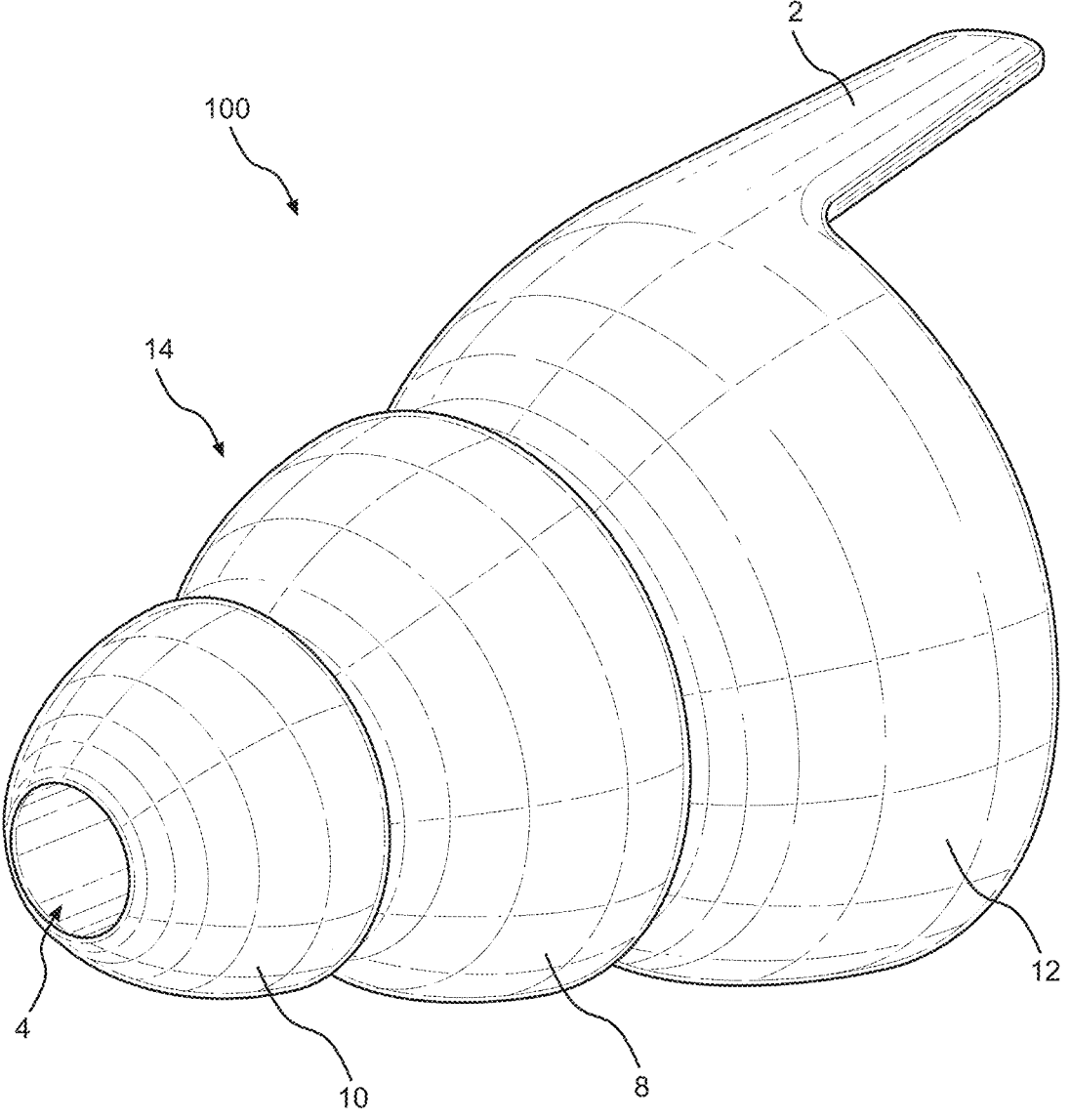
FIG. 1 illustrates a perspective view of an earplug, according to aspects of the present disclosure.

The invention now will be described more fully hereinafter with reference to the accompanying drawings, in which embodiments of the invention are shown. This invention may however be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," "upper" or "top," "left" or "right," "above" or "below," "front" or "rear," may be used herein to describe one element's relationship to another element as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. The numbers, ratios, percentages, and other values may include those that are ±5%, ±10%, ±25%, ±50%, ±75%, ±100%, ±200%, ±500%, or other ranges that do not detract from the spirit of the invention. The terms about, approximately, or substantially may include values known to those having ordinary skill in the art. If not known in the art, these terms may be considered to be in the range of up to +5%, ±10%, or other value higher than these ranges commonly accepted by those having ordinary skill in the art for the variable disclosed. Thus, embodiments of the present invention should not be construed as limited to the particular shapes of regions illustrated herein but are to include deviations in shapes that result, for example, from manufacturing. The invention illustratively disclosed herein suitably may be practiced in the absence of any elements that are not specifically disclosed herein. All patents, patent applications and non-patent literature cited through this Specification are hereby incorporated by reference in their entireties. References cited in an Information Disclosure Statement should not be construed as an admission that the cited reference comes from an area that is analogous or directly applicable to the invention, but rather that the reference is being cited out of an abundance of caution.

The present disclosure relates to earplugs incorporating glow-in-the-dark properties. In particular, the disclosure provides silicone earplugs that may include phosphorescent materials, allowing the earplugs to emit light in low-light conditions without the need for batteries or other power sources.

In some aspects, the earplugs may comprise a body made from a silicone material. The silicone material may include one or more phosphorescent compounds, such as zinc sulfide, strontium aluminate, or rare-earth metal chelates. These phosphorescent materials may absorb light when exposed to illumination and subsequently emit light over an extended period in dark environments.

The composition of the earplug material may include a base of polydimethylsiloxane (PDMS) combined with phosphorescent pigments. In some cases, the PDMS may constitute 80-90% of the composition, while the phosphorescent material may comprise 5-15%. Additional components such as silica fillers, curing agents, plasticizers, fluorescent dyes, and antimicrobial agents may be incorporated in various proportions to enhance the properties of the earplugs.

In certain aspects, the earplugs may include a sound-impeding filter designed to reduce the amplitude of sound waves entering the ear canal. The earplugs may also feature a layered design with multiple sections that gradually decrease in diameter towards the tip. In some cases, a fin or tab-like extension may be included to help secure the earplug in place within the ear.

The glow-in-the-dark feature of these earplugs may provide enhanced visibility and locatability in low-light conditions. This characteristic may be achieved without the addition of electronic components or power sources, potentially reducing the weight, complexity, and maintenance requirements associated with illuminated earplugs.

Referring to FIG. 1, an earplug device 100 is illustrated in a perspective view. The earplug may comprise a conical body 14 that tapers from a wider base to a narrower tip. In some aspects, the body 14 may feature a tiered design with multiple rounded sections decreasing in diameter towards the tip. As shown in FIG. 1 there is a narrow tip 10, a middle region 8, and a wide region 12. This tiered structure may aid in creating a secure fit within the ear canal and potentially enhance sound isolation.

The earplug may include a small circular opening 4 at the narrow end 10, which may serve as a pathway for sound transmission. In some cases, this opening may house a sound filter or other audio-modifying components.

A notable feature of the earplug may be a fin-like protrusion 2 extending from the upper portion of the main body.

The surface of the earplug may appear smooth and rounded and may be constructed from a soft, flexible material such as silicone. This design choice may enhance comfort and allow for a snug fit within the ear canal. In some aspects, the material may incorporate phosphorescent compounds, enabling the earplug to glow in low-light conditions.

The overall shape and structure is designed to be inserted into the ear canal. In some cases, the design may allow for customization of fit through interchangeable tip sizes or materials.

Figure 2:
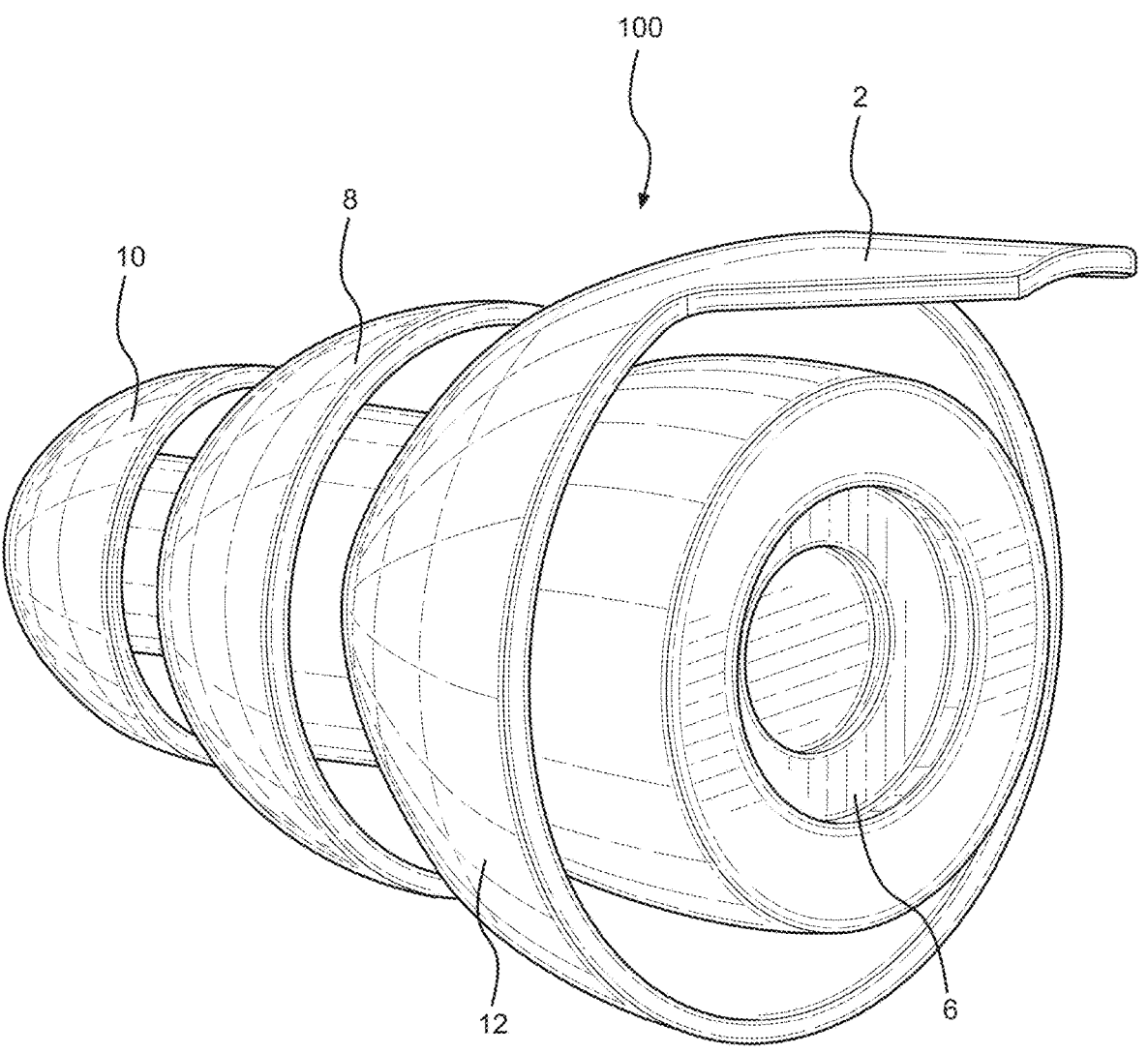
FIG. 2 illustrates another perspective view of the earplug of FIG. 1, according to an embodiment.

Referring to FIG. 2, another view of earplug device 100 is illustrated. The earplug may include a filter 6 mechanism designed to impede or reduce sound entering the ear. In some aspects, this filter mechanism may be positioned centrally within the earplug structure. The filter may be configured to selectively attenuate certain frequencies or reduce overall sound levels while still allowing necessary audio or environmental awareness.

Figure 3:
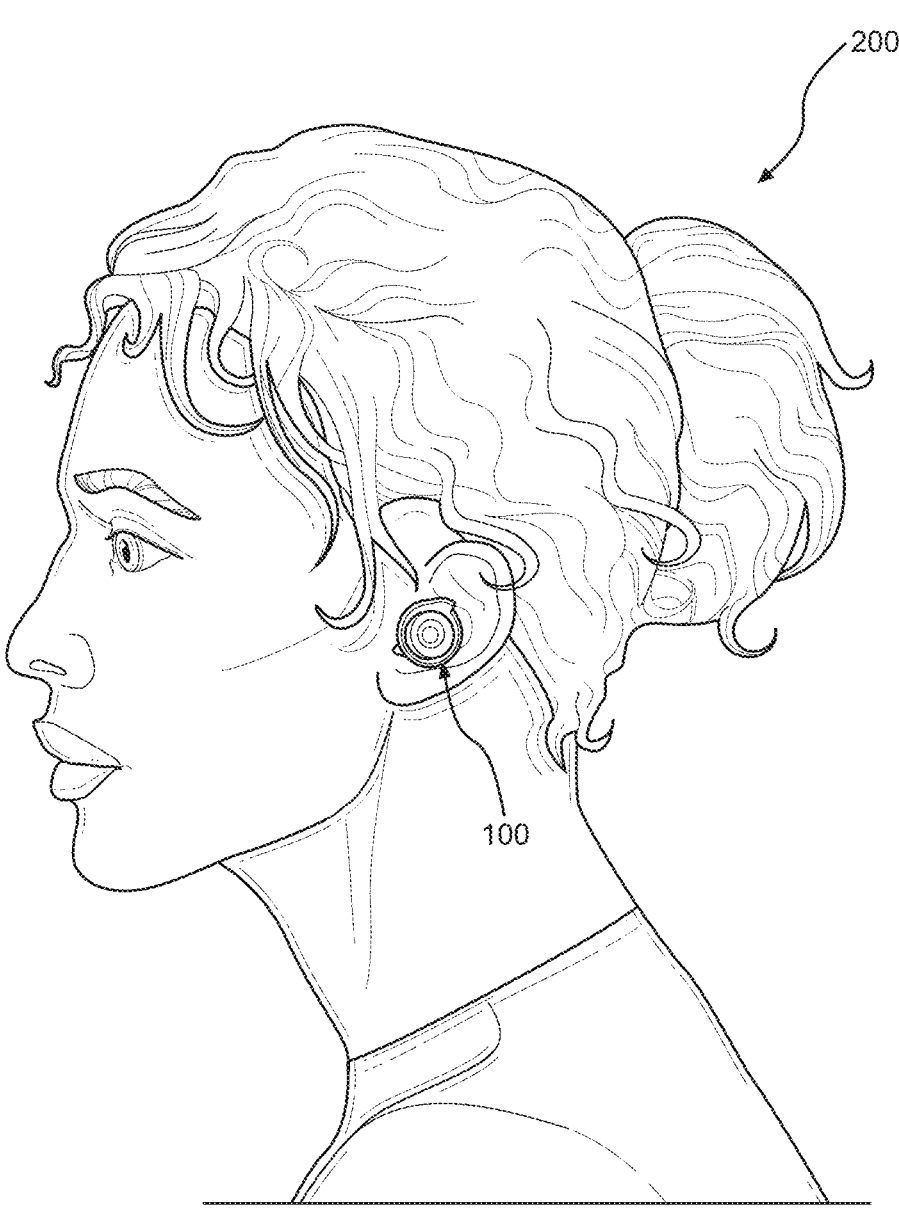
FIG. 3 illustrates an environmental view of the earplug of FIG. 1 used by a person.

Referring to FIG. 3, another view of the earplug device 100 is illustrated. Here the earplug device 100 is inside of a person's 200 ear.

The filter 6 mechanism may comprise various materials and designs to achieve desired sound attenuation properties. In some aspects, the filter may utilize acoustic mesh, foam, or other sound-absorbing materials. The specific composition and structure of the filter may be tailored to provide different levels of sound reduction or frequency response characteristics.

The structure surrounding the filter may be constructed from a flexible material, such as silicone or a similar elastomer. This design may allow the earplug to compress slightly when inserted into the ear canal, potentially improving comfort and fit. In some cases, the spiral structure may also serve to distribute pressure evenly around the ear canal, reducing discomfort during extended wear.

The earplug may also include additional internal components to support its functionality. In some aspects, these components may include channels for sound transmission, and structural supports.

The internal design of the earplug may be optimized to balance sound attenuation, comfort, and durability. In some cases, the materials and structures used may be selected to withstand repeated insertion and removal from the ear canal while maintaining their sound-impeding properties.

In some aspects, the earplug may be composed of a glow-in-the-dark material that incorporates phosphorescent or fluorescent compounds mixed with silicone. The glow-in-the-dark properties may be achieved through the use of various compounds, such as Zinc Sulfide (ZnS), Strontium Aluminate (SrAl2O4), phosphorescent pigments, rare-earth metal chelates, photochromic additives, or fluorescent dyes.

The composition of the earplug material may include specific percentages of components. In some cases, the silicone base material may comprise 80-90% of the total composition. Phosphorescent pigments may constitute 5-15% of the material. Additional components may include 2-5% silica, 1-3% curing agents, 0.5-2% plasticizers, 0.1-0.5% fluorescent dyes, and 0.05-0.1% antimicrobial agents.

The process of manufacturing the glow-in-the-dark earplug may involve several steps. Initially, photoluminescent pigments may be mixed into the silicone base material before curing. The silicone mixture may then be cured, which may involve heat treatment or the use of specific curing agents. In some aspects, a final surface treatment may be applied to enhance the durability and comfort of the earplug.

Zinc sulfide (ZnS) may be used as a phosphorescent material in some cases. ZnS may be doped with copper to enhance its glow-in-the-dark properties. The glow color of ZnS may vary depending on the doping element, with copper-doped ZnS typically emitting a green glow.

Strontium Aluminate ($SrAl2O4$) may be employed as an alternative phosphorescent material. $SrAl2O4$ may be doped with rare-earth metals such as europium and dysprosium to achieve brighter and longer-lasting glow properties. The glow color of $SrAl2O4$ may typically be green or blue.

In some aspects, phosphorescent pigments specifically compatible with silicone may be utilized. These pigments may be derived from Strontium Aluminate or Zinc Sulfide and may be available in various colors, including green, blue, yellow, and red.

Rare-earth metal chelates, such as europium complexes, may be incorporated into the earplug material in some cases. These compounds may be highly efficient at absorbing and emitting light, potentially providing a bright and stable glow in colors such as red or blue.

Photochromic additives may be used in some aspects to create earplugs that change color when exposed to light and subsequently glow in the dark. These additives may be embedded into the silicone and activated by specific light wavelengths, typically UV light.

Fluorescent dyes may be combined with phosphorescent materials in some cases to enhance the visible brightness of the glow. These dyes may absorb UV light and emit it as visible light, potentially making the glow more vibrant.

The manufacturing process may involve careful consideration of pigment dispersion, concentration, heat stability, and non-toxicity. Uniform dispersion of phosphorescent pigments within the silicone may be crucial for an even glow. The concentration of photoluminescent material may affect both the brightness and duration of the glow. Heat stability may be important during the curing process, and non-toxicity may be essential for skin contact.

In some aspects, the mixing process may involve incorporating the photoluminescent pigments into the silicone base material before curing. The silicone may then be cured, either by heat or with a curing agent, embedding the phosphorescent materials into the solidified silicone matrix. A final surface treatment may be applied in some cases to protect the phosphorescent layer and maintain smoothness and comfort.

The glow-in-the-dark silicone earplugs described in this disclosure may offer several advantages over traditional earplugs and other illuminated audio devices.

In some aspects, the incorporation of phosphorescent materials into the silicone body of the earplugs may provide enhanced visibility in low-light conditions without the need for batteries or electronic components. This feature may allow users to easily locate their earplugs in dimly lit environments, such as during nighttime use or in dark storage areas. The absence of electronic lighting components may result in a lighter, more compact design compared to earplugs with active illumination systems.

The use of silicone as the base material for the earplugs may offer benefits in terms of comfort and fit. Silicone may be soft and flexible, potentially allowing the earplugs to conform to the unique shape of each user's ear canal. This adaptability may contribute to a more secure and comfortable fit, which may be particularly advantageous during physical activities or extended wear periods.

In some cases, the layered design of the earplug body, featuring multiple sections that gradually decrease in diameter towards the tip, may provide improved sound isolation. This design may help create a more effective seal within the ear canal, potentially enhancing the audio experience by reducing external noise interference. The inclusion of a sound-impeding filter may further contribute to sound quality by selectively attenuating certain frequencies or reducing overall sound levels while still allowing for necessary environmental awareness.

The fin 2 or tab-like extension included in some embodiments may offer additional stability and security. This feature may help keep the earplugs in place during various activities, potentially reducing the need for frequent adjustments and improving overall user experience and is also useful for grabbing onto, in order to remove the earplug 100 from the ear.

The composition of the earplug material, which may include additional components such as silica fillers, curing agents, plasticizers, and antimicrobial agents, may contribute to enhanced durability and hygiene. These additives may help the earplugs maintain their shape and properties over time, while potentially reducing the risk of bacterial growth associated with frequent skin contact.

In some aspects, the manufacturing process described for these earplugs may allow for customization of glow colors and intensities. The ability to incorporate different phosphorescent compounds or combinations of materials may provide options for users with varying preferences or needs. This customization potential may extend to the physical design of the earplugs as well, with the possibility of interchangeable tip sizes or materials to accommodate different ear anatomies.

The glow-in-the-dark feature may also serve a safety function in certain scenarios. For example, the visibility of the earplugs in low-light conditions may be beneficial for users engaging in outdoor activities during dawn, dusk, or nighttime hours. This added visibility may contribute to user safety in environments where being seen is important.

In some aspects, the earplug material may incorporate a blend of different phosphorescent compounds to achieve specific glow characteristics. For example, a combination of Zinc Sulfide and strontium aluminate may be used to create a glow that is both bright and long-lasting. The Zinc Sulfide may provide an initial intense glow, while the Strontium Aluminate may contribute to extended luminescence over several hours.

The silicone base material may be modified to include additional polymers or elastomers to enhance specific properties. In some cases, a small percentage of polyurethane may be added to the silicone mixture to improve durability and tear resistance. This hybrid material may retain the flexibility and comfort of silicone while providing increased resistance to wear and tear from repeated use.

In certain embodiments, the earplug material may incorporate thermochromic pigments in addition to phosphorescent compounds. These thermochromic additives may cause the earplugs to change color in response to body heat when inserted into the ear canal. This feature may provide a visual indication that the earplugs are properly seated and may also serve as an interesting aesthetic element.

The earplug material may include phase-change materials (PCMs) in some cases. These PCMs may absorb, store, and release heat, potentially providing a cooling effect during wear. This feature may enhance comfort during extended use or in warm environments.

In some aspects, the earplug material may incorporate nanoparticles to enhance specific properties. For example, silver nanoparticles may be added to provide antimicrobial properties, potentially reducing the risk of ear infections. Alternatively, carbon nanotubes may be incorporated to improve the mechanical strength and durability of the earplugs without significantly increasing their weight.

The earplug material may include moisture-wicking additives in certain embodiments. These additives may help to draw sweat and moisture away from the ear canal, potentially improving comfort and reducing the risk of irritation during extended wear or physical activities.

In some cases, the earplug material may incorporate piezoelectric elements. These elements may generate small amounts of electrical energy in response to mechanical stress, such as the insertion or removal of the earplugs. This energy may be used to power small LED indicators or to enhance the glow-in-the-dark properties of the phosphorescent materials.

The earplug material may include shape memory polymers in certain aspects. These polymers may allow the earplugs to temporarily deform for easy insertion into the ear canal and then return to their original shape to create a secure fit. This feature may enhance both comfort and sound isolation.

In some embodiments, the earplug material may incorporate photochromic compounds that change color when exposed to UV light. This feature may allow the earplugs to change appearance when moving between indoor and outdoor environments, potentially serving as a UV exposure indicator for users.

The earplug material may include thermally conductive additives in certain aspects. These additives may help to dissipate heat generated by any electronic components within the earplugs, potentially improving comfort during extended use and prolonging the lifespan of the electronics.

In some aspects, the method of using the glow-in-the-dark earplugs may involve a preparatory step of exposing the earplugs to light before use. This exposure may activate the phosphorescent materials incorporated into the silicone body of the earplugs, allowing them to emit a visible glow in low-light conditions.

The duration of light exposure may vary depending on the specific phosphorescent materials used in the earplug construction. In some cases, exposing the earplugs to bright light for 5-10 minutes may be sufficient to achieve a noticeable glow. However, longer exposure times, such as 15-30 minutes, may result in a brighter and more prolonged glow effect.

Various light sources may be used to charge the phosphorescent materials in the earplugs. Natural sunlight may be particularly effective due to its broad spectrum of wavelengths. Alternatively, artificial light sources such as LED lamps, fluorescent bulbs, or UV lights may also be used. In some instances, specialized charging stations or cases equipped with built-in lights may be provided to conveniently prepare the earplugs for use.

After the light exposure period, the earplugs may be ready for insertion into the ear canal. The user may gently compress the earplug and insert it into the ear, allowing the flexible silicone material to conform to the shape of the ear canal. The layered design of the earplug body may assist in creating a secure and comfortable fit.

In some cases, the user may need to adjust the position of the earplug to achieve optimal comfort and sound isolation. The fin or tab-like extension, if present, may be positioned to fit into the folds of the outer ear, providing additional stability. The user may gently twist or push the earplug to ensure it is properly seated within the ear canal.

Once inserted, the glow-in-the-dark earplugs may provide both audio functionality and enhanced visibility in low-light conditions. The phosphorescent glow may make the earplugs easier to locate when not in use, potentially reducing the risk of misplacement or loss. Additionally, the glow may serve as a visual indicator of the earplug's presence, which may be beneficial in certain social or professional settings.

The method of use may also include periodic re-exposure to light to maintain the glow effect. Depending on the specific phosphorescent materials used, the glow intensity may gradually diminish over time. Users may choose to recharge the glow effect by exposing the earplugs to light between uses or during breaks in extended listening sessions.

In some aspects, the method of manufacturing the glow-in-the-dark silicone earplugs may involve several key steps. The process may begin with the preparation of the silicone base material, which may include mixing polydimethylsiloxane (PDMS) with other additives to achieve the desired properties. The phosphorescent materials may then be incorporated into this base mixture, potentially using specialized mixing equipment to ensure uniform distribution.

The combined silicone and phosphorescent mixture may be degassed to remove any air bubbles that could affect the final product quality. This step may involve placing the mixture in a vacuum chamber or using other degassing techniques. Once the mixture is free of air bubbles, it may be ready for molding.

In some cases, the earplug molds may be prepared with a release agent to facilitate easy removal of the finished product. The silicone mixture may then be carefully injected or poured into these molds, which may be designed to create the layered structure and fin extension of the earplugs. The molds may also incorporate features to form the channel for the sound-impeding filter.

The molded earplugs may then undergo a curing process, which may involve heat treatment or the use of specific curing agents. The duration and conditions of this curing process may be carefully controlled to ensure optimal cross-linking of the silicone polymer chains and proper integration of the phosphorescent materials.

After curing, the earplugs may be removed from the molds and inspected for any defects or imperfections. In some aspects, a post-curing treatment may be applied to enhance the mechanical properties and durability of the earplugs. This may involve additional heat treatment or exposure to specific wavelengths of light to fully activate the phosphorescent compounds.

The sound-impeding filters may be inserted into the designated channels within the earplug bodies. These filters may be carefully positioned to ensure proper functionality without compromising the integrity of the silicone structure. In some cases, a small amount of adhesive may be used to secure the filters in place.

The final steps of the manufacturing process may include cleaning the earplugs to remove any residual mold release agents or other contaminants. A quality control inspection may be performed to verify the glow-in-the-dark properties, structural integrity, and overall conformity to design specifications. The earplugs may then be packaged, potentially with instructions for use and care, ready for distribution to end-users.

A number of implementations have been described. Nevertheless, it will be understood that various modifications may be made without departing from the spirit and scope of the disclosure. Accordingly, other implementations are within the scope of the following claims.

CLAUSES

1. An earplug device, comprising: a body made of a silicone material, wherein the silicone material comprises a phosphorescent material that causes the earplug to glow in the dark after being exposed to light; and a sound-impeding filter positioned within the body.

2. The earplug device of clause 1, wherein the phosphorescent material is selected from the group consisting of zinc sulfide, strontium aluminate, and rare-earth metal chelates.

3. The earplug device of clause 2, wherein the phosphorescent material comprises strontium aluminate doped with europium and dysprosium.

4. The earplug device of clause 1, wherein the silicone material comprises 80-90% polydimethylsiloxane and 5-15% of the phosphorescent material.

5. The earplug device of clause 1, further comprising a fin extending from the body, the fin configured to fit into folds of an outer ear to secure the earplug device in place.

6. The earplug device of clause 1, wherein the body has a layered design with multiple sections that gradually decrease in diameter towards a tip of the earplug device.

7. The earplug device of clause 6, wherein the sound-impeding filter is positioned within a narrow channel at the tip of the earplug device, and wherein the earplug device further comprises 2-5% silica as a reinforcing filler, 1-3% of a curing agent, 0.5-2% of a plasticizer, 0.1-0.5% of a fluorescent dye, and 0.05-0.1% of an antimicrobial agent.

8. A method of using an earplug device, comprising: exposing an earplug device to light, wherein the earplug device comprises a body made of a silicone material incorporating a phosphorescent material; inserting the earplug device into an ear canal; and blocking sound using a sound-impeding filter positioned within the body of the earplug device.

9. The method of clause 8, wherein exposing the earplug device to light comprises exposing the earplug device to natural sunlight or artificial light for a duration of 5 to 30 minutes.

10. The method of clause 9, wherein the phosphorescent material is selected from the group consisting of zinc sulfide, strontium aluminate, and rare-earth metal chelates.

11. The method of clause 10, wherein inserting the earplug device into the ear canal comprises positioning a fin extending from the body of the earplug device into folds of an outer ear to secure the earplug device in place.

12. The method of clause 11, wherein blocking sound comprises reducing the amplitude of sound waves entering the ear canal using the sound-impeding filter.

13. The method of clause 12, wherein the body of the earplug device has a layered design with multiple sections that gradually decrease in diameter towards a tip of the earplug device.

14. The method of clause 13, wherein the silicone material of the earplug device comprises 80-90% polydimethylsiloxane and 5-15% of the phosphorescent material, wherein the phosphorescent material comprises strontium aluminate doped with europium and dysprosium, wherein the earplug device further comprises 2-5% silica as a reinforcing filler, 1-3% of a curing agent, 0.5-2% of a plasticizer, 0.1-0.5% of a fluorescent dye, and 0.05-0.1% of an antimicrobial agent, and wherein the sound-impeding filter is positioned within a narrow channel at the tip of the earplug device.

15. A method of manufacturing an earplug device, comprising: mixing a silicone material with a phosphorescent material to form a mixture; molding the mixture into an earplug body shape; and curing the molded mixture.

16. The method of clause 15, wherein the phosphorescent material is selected from the group consisting of zinc sulfide, strontium aluminate, and rare-earth metal chelates.

17. The method of clause 16, wherein mixing the silicone material with the phosphorescent material comprises combining 80-90% polydimethylsiloxane and 5-15% of the phosphorescent material.

18. The method of clause 17, further comprising adding 2-5% silica as a reinforcing filler, 1-3% of a curing agent, 0.5-2% of a plasticizer, 0.1-0.5% of a fluorescent dye, and 0.05-0.1% of an antimicrobial agent to the mixture.

19. The method of clause 18, wherein molding the mixture into an earplug body shape comprises forming a layered design with multiple sections that gradually decrease in diameter towards a tip of the earplug device, and forming a fin extending from the body configured to fit into folds of an outer ear.

20. The method of clause 19, wherein inserting the sound-impeding filter comprises positioning the filter within a narrow channel at the tip of the earplug device, and wherein the phosphorescent material comprises strontium aluminate doped with europium and dysprosium.

I claim:

1. An earplug device, comprising:
a body made of a silicone material, wherein the silicone material comprises a phosphorescent material that causes the earplug to glow after being exposed to light; and a sound-impeding filter positioned within the body, wherein the body has a layered design with multiple sections that gradually decrease in diameter towards a tip of the earplug device, and wherein the sound-impeding filter is positioned within a narrow channel at the tip of the earplug device, and wherein the earplug device further comprises 2-5% silica as a reinforcing filler, 1-3% of a curing agent, 0.5-2% of a plasticizer, 0.1-0.5% of a fluorescent dye, and 0.05-0.1% of an antimicrobial agent.

2. The earplug device of claim 1, wherein the phosphorescent material is selected from the group consisting of zinc sulfide, strontium aluminate, and rare-earth metal chelates.

3. The earplug device of claim 2, wherein the phosphorescent material comprises strontium aluminate doped with europium and dysprosium.

4. The earplug device of claim 1, wherein the silicone material comprises 80-90% polydimethylsiloxane and 5-15% of the phosphorescent material.

5. The earplug device of claim 1, further comprising a fin extending from the body, the fin configured to fit into folds of an outer ear to secure the earplug device in place.

6. A method of manufacturing an earplug device, comprising:

mixing a silicone material with a phosphorescent material to form a mixture;

molding the mixture into an earplug body shape; and curing the molded mixture;

wherein the phosphorescent material is selected from the group consisting of zinc sulfide, strontium aluminate, and rare-earth metal chelates;

wherein mixing the silicone material with the phosphorescent material comprises combining 80-90% polydimethylsiloxane and 5-15% of the phosphorescent material;

further comprising adding 2-5% silica as a reinforcing filler, 1-3% of a curing agent, 0.5-2% of a plasticizer, 0.1-0.5% of a fluorescent dye, and 0.05-0.1% of an antimicrobial agent to the mixture.

7. The method of claim 6, wherein molding the mixture into an earplug body shape comprises forming a layered design with multiple sections that gradually decrease in diameter towards a tip of the earplug device.

8. The method of claim 7, wherein inserting the sound-impeding filter comprises positioning the filter within a narrow channel at the tip of the earplug device, and wherein the phosphorescent material comprises strontium aluminate doped with europium and dysprosium.

9. A method of using an earplug device, comprising:

exposing an earplug device to light, wherein the earplug device comprises a body made of a silicone material incorporating a phosphorescent material, wherein exposing the earplug device to light comprises exposing the earplug device to natural sunlight or artificial light for a duration of 5 to 30 minutes, wherein the phosphorescent material is selected from the group consisting of zinc sulfide, strontium aluminate, and rare-earth metal chelates;

inserting the earplug device into an ear canal, wherein inserting the earplug device into the ear canal comprises positioning a fin extending from the body of the earplug device into folds of an outer ear to secure the earplug device in place; and blocking sound using a sound-impeding filter positioned within the body of the earplug device, wherein blocking sound comprises reducing an amplitude of sound waves entering the ear canal using the sound-impeding filter, wherein the body of the earplug device has a layered design with multiple sections that gradually decrease in diameter towards a tip of the earplug device, wherein the silicone material of the earplug device comprises 80-90% polydimethylsiloxane and 5-15% of the phosphorescent material, wherein the phosphorescent material comprises strontium aluminate doped with europium and dysprosium, wherein the earplug device further comprises 2-5% silica as a reinforcing filler, 1-3% of a curing agent, 0.5-2% of a plasticizer, 0.1-0.5% of a fluorescent dye, and 0.05-0.1% of an antimicrobial agent, and wherein the sound-impeding filter is positioned within a narrow channel at the tip of the earplug device.

* * * * *